(12) United States Patent
Stevenson et al.

(10) Patent No.: US 8,761,895 B2
(45) Date of Patent: Jun. 24, 2014

(54) RF ACTIVATED AIMD TELEMETRY TRANSCEIVER

(75) Inventors: Robert A. Stevenson, Canyon Country, CA (US); Christine A. Frysz, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 976 days.

(21) Appl. No.: 12/719,630

(22) Filed: Mar. 8, 2010

(65) Prior Publication Data

US 2010/0185263 A1  Jul. 22, 2010

Related U.S. Application Data

(63) Continuation-in-part of application No. 12/566,223, filed on Sep. 24, 2009, now Pat. No. 8,253,555, and a continuation-in-part of application No. 12/407,402, filed on Mar. 19, 2009, now Pat. No. 8,195,295.

(60) Provisional application No. 61/150,061, filed on Feb. 5, 2009, provisional application No. 61/144,102, filed on Jan. 12, 2009, provisional application No. 61/116,094, filed on Nov. 19, 2008, provisional application No. 61/038,382, filed on Mar. 20, 2008.

(51) Int. Cl.
*A61N 1/08* (2006.01)

(52) U.S. Cl.
USPC .............................................. 607/60; 607/30

(58) Field of Classification Search
USPC ............. 607/30, 31, 32, 59, 60; 600/301, 302
See application file for complete search history.

(56) References Cited

U.S. PATENT DOCUMENTS

| | | |
|---|---|---|
| 3,681,612 A | 8/1972 | Vogl et al. |
| 3,745,430 A | 7/1973 | Lunquist et al. |
| 4,376,441 A | 3/1983 | Duncan |
| 4,424,551 A | 1/1984 | Stevenson et al. |
| 4,846,158 A | 7/1989 | Teranishi |
| 4,858,064 A | 8/1989 | Sagawa et al. |
| 5,268,810 A | 12/1993 | DiMarco et al. |
| 5,331,505 A | 7/1994 | Wilheim |
| 5,333,095 A | 7/1994 | Stevenson et al. |
| 5,336,158 A | 8/1994 | Huggins et al. |
| 5,450,090 A | 9/1995 | Gels et al. |
| 5,491,300 A | 2/1996 | Huppenthal et al. |
| 5,493,259 A | 2/1996 | Blalock et al. |
| 5,620,476 A | 4/1997 | Truex et al. |
| 5,650,759 A | 7/1997 | Hittman et al. |
| 5,683,435 A | 11/1997 | Truex et al. |
| 5,757,252 A | 5/1998 | Cho et al. |

(Continued)

FOREIGN PATENT DOCUMENTS

| | | |
|---|---|---|
| EP | 0 534 782 A1 | 3/1983 |
| EP | 0 619 101 A1 | 10/1994 |

(Continued)

*Primary Examiner* — Eric D. Bertram
*Assistant Examiner* — Pamela M Bays
(74) *Attorney, Agent, or Firm* — Michael F. Scalise

(57) ABSTRACT

A telemetry wake-up circuit is electrically disposed between a telemetry transceiver associated with an AIMD, and an RF tag. The RF tag may be remotely interrogated to generate a signal to which the telemetry wake-up circuit is responsive to switch the telemetry transceiver from a sleep mode to an active telemetry mode. In the sleep mode, the telemetry transceiver draws less than 25,000 nanoamperes from the AIMD, and preferably less than 500 nanoamperes.

27 Claims, 8 Drawing Sheets

(56) References Cited

U.S. PATENT DOCUMENTS

| | | |
|---|---|---|
| 5,765,779 A | 6/1998 | Hancock et al. |
| 5,782,891 A | 7/1998 | Hassler et al. |
| 5,822,174 A | 10/1998 | Yamate et al. |
| 5,855,609 A | 1/1999 | Knapp |
| 5,905,627 A | 5/1999 | Brendel et al. |
| 5,959,336 A | 9/1999 | Barsan |
| 5,973,906 A | 10/1999 | Stevenson et al. |
| 5,973,907 A | 10/1999 | Reed |
| 6,137,161 A | 10/2000 | Gilliland et al. |
| 6,146,743 A | 11/2000 | Haq et al. |
| 6,216,038 B1 | 4/2001 | Hartlaub et al. |
| 6,259,937 B1 | 7/2001 | Schulman et al. |
| 6,275,369 B1 | 8/2001 | Stevenson et al. |
| 6,342,839 B1 | 1/2002 | Curkendall et al. |
| 6,373,673 B1 | 4/2002 | Anthony |
| 6,375,780 B1 | 4/2002 | Tuttle et al. |
| 6,424,234 B1 | 7/2002 | Stevenson |
| 6,456,481 B1 | 9/2002 | Stevenson |
| 6,459,935 B1 | 10/2002 | Piersma |
| 6,473,314 B1 | 10/2002 | Custer et al. |
| 6,529,103 B1 | 3/2003 | Brendel et al. |
| 6,566,978 B2 | 5/2003 | Stevenson et al. |
| 6,660,116 B2 | 12/2003 | Wolf et al. |
| 6,735,479 B2 | 5/2004 | Fabian et al. |
| 6,765,779 B2 | 7/2004 | Stevenson et al. |
| 6,765,780 B2 | 7/2004 | Brendel et al. |
| 6,806,806 B2 | 10/2004 | Anthony |
| 6,957,107 B2 | 10/2005 | Rogers et al. |
| 7,017,822 B2 | 3/2006 | Aisenbrey |
| 7,038,900 B2 | 5/2006 | Stevenson et al. |
| 7,110,227 B2 | 9/2006 | Anthony et al. |
| 7,113,387 B2 | 9/2006 | Stevenson et al. |
| 7,199,995 B2 | 4/2007 | Stevenson |
| 7,236,834 B2 | 6/2007 | Christopherson et al. |
| 7,240,833 B2 | 7/2007 | Zarembo |
| 7,301,748 B2 | 11/2007 | Anthony et al. |
| 7,310,216 B2 | 12/2007 | Stevenson et al. |
| 7,322,832 B2 | 1/2008 | Kronich et al. |
| 7,327,553 B2 | 2/2008 | Brendel |
| 7,333,013 B2 | 2/2008 | Berger |
| 7,363,090 B2 | 4/2008 | Halperin |
| 7,423,860 B2 | 9/2008 | Anthony et al. |
| 7,428,136 B2 | 9/2008 | Barnett |
| 7,433,168 B2 | 10/2008 | Anthony |
| 7,436,672 B2 | 10/2008 | Ushijima et al. |
| 7,439,449 B1 | 10/2008 | Kumar et al. |
| 7,446,996 B2 | 11/2008 | Togashi |
| 7,450,396 B2 | 11/2008 | Ye et al. |
| 7,479,108 B2 | 1/2009 | Rini et al. |
| 2002/0151770 A1 | 10/2002 | Noll et al. |
| 2003/0114897 A1* | 6/2003 | Von Arx et al. ............ 607/60 |
| 2003/0229383 A1* | 12/2003 | Whitehurst et al. ........ 607/60 |
| 2005/0043594 A1* | 2/2005 | Dinsmoor et al. ......... 600/300 |
| 2005/0165317 A1* | 7/2005 | Turner et al. .............. 600/486 |
| 2005/0201039 A1 | 9/2005 | Stevenson et al. |
| 2006/0032665 A1 | 2/2006 | Ice |
| 2006/0085043 A1 | 4/2006 | Stevenson |
| 2006/0212096 A1 | 9/2006 | Stevenson |
| 2007/0112398 A1 | 5/2007 | Stevenson |
| 2007/0123949 A1 | 5/2007 | Dabney et al. |
| 2007/0203529 A1 | 8/2007 | Iyer et al. |
| 2007/0288058 A1 | 12/2007 | Halperin et al. |
| 2008/0048855 A1 | 2/2008 | Berger |
| 2008/0049376 A1 | 2/2008 | Stevenson |
| 2008/0049410 A1 | 2/2008 | Kawaguchi et al. |
| 2008/0065181 A1 | 3/2008 | Stevenson |
| 2008/0071313 A1 | 3/2008 | Stevenson |
| 2008/0116997 A1 | 5/2008 | Dabney |
| 2008/0132987 A1 | 6/2008 | Westlund |
| 2008/0158746 A1 | 7/2008 | Anthony et al. |
| 2008/0161886 A1 | 7/2008 | Stevenson |
| 2008/0195180 A1 | 8/2008 | Stevenson et al. |
| 2000/8329622 | 10/2008 | Hsu et al. |
| 2008/0247111 A1 | 10/2008 | Anthony et al. |
| 2008/0247116 A1 | 10/2008 | Kawano et al. |
| 2008/0247117 A1 | 10/2008 | Elam et al. |
| 2008/0264685 A1 | 10/2008 | Park et al. |
| 2008/0277153 A1 | 11/2008 | Teshome et al. |
| 2009/0107717 A1 | 4/2009 | Hsu et al. |
| 2009/0128976 A1 | 5/2009 | Anthony |
| 2009/0139760 A1 | 6/2009 | Tanaka |
| 2009/0180237 A1 | 7/2009 | Hou et al. |
| 2009/0187229 A1 | 7/2009 | Lavie |

FOREIGN PATENT DOCUMENTS

| | | |
|---|---|---|
| JP | 6176962 | 6/1994 |
| JP | 2001068958 | 3/2001 |
| JP | 2004254257 | 9/2004 |
| JP | 2004289760 | 10/2004 |
| JP | 2005117606 | 4/2005 |
| JP | 2007129565 | 11/2005 |
| WO | WO 9611722 A1 | 4/1996 |

* cited by examiner

RF ACTIVATED AIMD TELEMETRY TRANSCEIVER

CROSS-REFERENCE TO RELATED APPLICATIONS

This a application in a continuation-in-part of application Ser. No. 12/566,223, filed on Sep. 24, 2009, now U.S. Pat. No. 8,253,555, which is a continuation-in-part of application Ser. No. 12/407,402, filed on Mar. 19, 2009, now U.S. Pat. No. 8,195,295. This application also claims priority from provisional application Ser. No. 61/150,061, filed on Feb. 5, 2009, provisional application Ser. No. 61/144,102, filed on Jan. 12, 2009, provisional application Ser. No. 61/116,094, filed on Nov. 19, 2009, and provisional application Ser. No. 61/038,382, filed on Mar. 20, 2008.

BACKGROUND OF THE INVENTION

The present invention relates generally to telemetry transceivers associated with active implantable medical devices (AIMDs) and related components. More particularly, the present invention relates to AIMD RF telemetry circuits having radio frequency identification (RFID) controllable wake-up features.

FIGS. 1 and 2 provide a background for better understanding of the present invention. FIG. 1 is a wire formed diagram of a generic human body showing a number of implanted medical devices. 100A represents a family of hearing devices which can include the group of cochlear implants, piezoelectric sound bridge transducers and the like. 100B represents a variety of neurostimulators and brain stimulators. Neurostimulators are used to stimulate the Vagus nerve, for example, to treat epilepsy, obesity and depression. Brain stimulators are pacemaker-like devices and include electrodes implanted deep into the brain for sensing the onset of the seizure and also providing electrical stimulation to brain tissue to prevent the seizure from actually occurring. The lead wires associated with a deep brain stimulator are often placed using real time MRI imaging. 100C shows a cardiac pacemaker which is well-known in the art. 100D includes the family of left ventricular assist devices (LVAD's) and artificial hearts. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator or even a ventricular assist device.

FIG. 2 is a prior art cardiac pacemaker 100C. A cardiac pacemaker typically has an electromagnetically shielded and hermetically sealed housing 102 which is generally constructed from titanium, stainless steel or the like. It also has a plastic or Techothane header block 104 which houses ISO standard IS-1 type connectors 106, 108. In the past, AIMDs, in particular pacemakers, ICDs and neurostimulators, embodied close-coupled telemetry circuits. The purpose of telemetry is so that the AIMD could be interrogated or even reprogrammed after implantation. For example, it is common to monitor battery status, patient biologic conditions and the like, through telemetry. In addition, an external telemetry programmer can be used to re-program the AIMD, for example, and put it into different modes of operation. In the past, for pacemakers and ICDs the telemetry was inductive (low frequency magnetic) and close coupled. In this older art it was typical that the AIMD would have a multiple turn wire antenna within its titanium housing. There were even AIMDs that used an external loop antenna of this type. To interrogate or re-program the AIMD, the physician or other medical practitioners would bring a wand, with a similar antenna embedded in it, very close to the AIMD. For example, for a typical pacemaker application the telemetry wand would be placed directly over the implant. The wand is/was connected with wiring to the external programmer. The medical practitioner would move the wand around until the "sweet-spot" was located. Once the wand is located in the "sweet-spot," a communication link is established between the multiple turn wire antenna implanted in the AIMD and a similar multiple turn wire antenna located inside the telemetry wand. The external programmer would then become active and electrograms and other important information would be displayed. Typically the telemetry wand would be placed either against or very close to the patient's skin surface or at most a few centimeters away.

In the last few years, distance RF telemetry has become increasingly common. For distance telemetry, for example for a cardiac pacemaker 100C, there would be a high frequency antenna that would be located outside of the AIMD shielded titanium housing 102. This could, for example, be placed in or adjacent to the AIMD plastic header block 104. The external antenna would communicate with an external programmer that would have its own RF transceiver. A typical band for such communication is in the 402 to 405 MHz frequency range (known as the MICS band). There are other bands that may be used for RF telemetry including gigahertz frequencies. A problem with such prior art RF distance telemetry circuits is that energy consumption is high because the receiver circuitry must be on all the time.

The Zarlink chip has provided one solution to this problem. The Zarlink chip uses higher frequencies (in the gigahertz range) to wake-up the lower frequency RF telemetry circuit which is generally in the MICS band. The higher frequency GHz receiver of the Zarlink chip is very energy efficient, however the device or chip still consumes an amount of idling energy from the AIMD battery to always be alert for its wake-up call. In general, this current draw link is in the order of 250 picoamperes (250,000 nanoamperes). This is still a significant amount of idling current over the life of the pacemaker and generally shortens the pacemaker life by at least one month.

Accordingly, there is a need for an RF activated AIMD telemetry transceiver that includes means responsive to a signal from an RF transmitter to place an AIMD telemetry transceiver into its active telemetry mode. During a sleep mode for the AIMD telemetry transceiver, the system should draw a minimal amount of power from the AIMD, on the order of 25,000 nanoamperes or less, and preferably 500 nanoamperes or less. A circuit connection is provided which would be responsive to a signal from the RF tag to place the telemetry transceiver into its active telemetry mode. Preferably, the entire wake-up feature would be externally powered by, for example, the energy coupled from an external/remote RF reader. Once the AIMD telemetry transceiver is placed into its active mode, a feature is needed wherein the AIMD telemetry circuit can go back into its quiescent sleep mode. Accordingly, there is need for circuits and/or programmer commands to place the AIMD telemetry receiver back into a sleep mode after a set amount of time or after a receipt of a signal from the external programmer. The present invention fulfills these needs and provides other related advantages.

SUMMARY OF THE INVENTION

The present invention relates to an RF (radio frequency) activated AIMD (active implantable medical device) telemetry transceiver, generally comprising: (1) a telemetry transceiver associated with the AIMD, (2) a passive RF tag associated with the telemetry transceiver, and (3) a telemetry wake-up circuit electrically disposed between the telemetry transceiver and the RF tag. The telemetry transceiver has an active telemetry mode wherein the telemetry transceiver is powered by the AIMD, and a sleep mode. The telemetry wake-up circuit is responsive to a signal from the RF tag to place the telemetry transceiver into the active telemetry mode.

In a preferred embodiment, the RF tag comprises a passive RF or RFID chip and an antenna. The RF chip typically includes at least four terminals, and the antenna preferably comprises a biocompatible antenna. As shown, the RF chip is disposed within a hermetic package to prevent contact between the RF chip and body tissue or body fluids. The RF chip may be disposed within a housing for the AIMD which, thus, serves as the hermetic package. Alternatively, the RF tag may be disposed within its own hermetic package and disposed within the header block for the AIMD. The RF chip is activated by a remote source, such as an RF transmitter such as an RFID reader/interrogator, which may be a wireless unit, or integrated into or tethered to an AIMD programmer. The signal from the RF tag to place the telemetry transceiver into the active telemetry mode is generated in response to activation of the RF chip.

The telemetry wake-up circuit typically comprises a microelectronic switch. The microelectronic switch may comprise a bipolar junction transistor (BJT) switch, a field effect transistor (FET) switch, a MOSFET switch, a MEMS switch, a unijunction transistor switch, a silicon-controlled rectifier (SCR) switch, a PIN diode switch, a P-N junction transistor switch, a P-N-P transistor switch, or an N-P-N junction switch.

In its sleep mode, the telemetry transceiver draws less than 25,000 nanoamperes from the AIMD, and preferably less than 500 nanoamperes. In one embodiment, a timing circuit is provided for switching the telemetry transceiver from the active telemetry mode to the sleep mode. The timing circuit is re-set responsive to the signal from the RF tag to place the telemetry transceiver into the active telemetry mode. In another embodiment, the telemetry transceiver includes a sleep mode circuit responsive to a signal from the RF tag or a remote RF or inductive low frequency magnetic coupling source, for switching the telemetry transceiver from the active telemetry mode to the sleep mode.

In the active telemetry mode, the telemetry transceiver communicates with the remote RF or inductive low frequency magnetic coupling source. This remote source may comprise an AIMD programmer.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
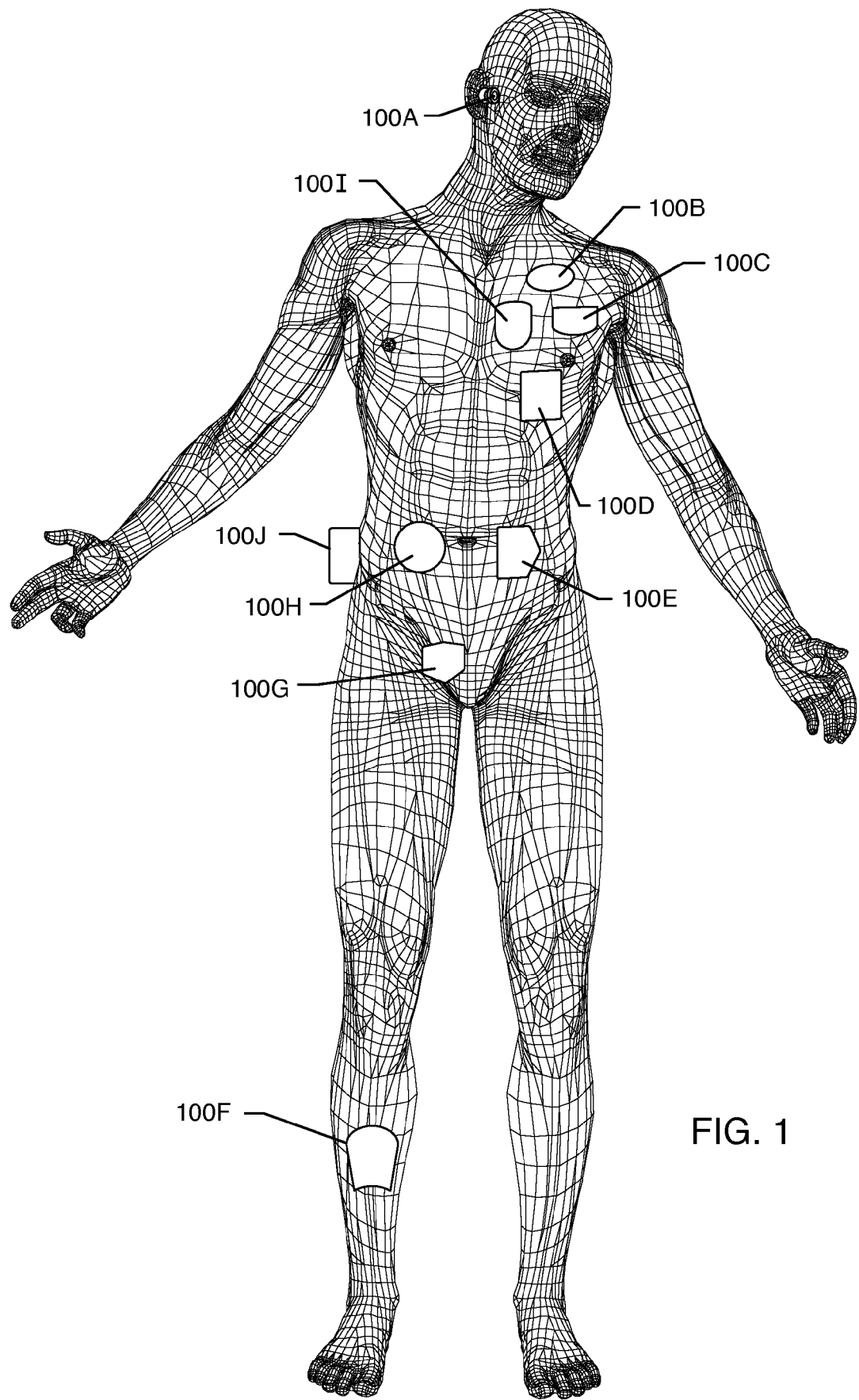
FIG. 1 is a wire formed diagram of a generic human body showing a number of implanted medical devices.

The present invention, in a broad sense, relates to an RF activated AIMD telemetry transceiver which includes (1) a telemetry transceiver associated with an AIMD, having an active telemetry mode wherein the telemetry transceiver is powered by the AIMD, and a sleep mode; (2) a passive RF tag associated with the telemetry transceiver; and (3) a telemetry wake-up circuit electrically disposed between the telemetry transceiver and the passive RF tag. The telemetry wake-up circuit is responsive to a signal from the RF tag to place the telemetry transceiver in the active telemetry mode. In a preferred embodiment, the AIMD transceiver has a timer wherein it returns to its sleep mode after a predetermined amount of time. As an alternative, a remote AIMD programmer may send a signal to the AIMD telemetry antenna and associated transceiver telling it to turn off and return to its sleep mode.

In a preferred embodiment, the remote AIMD programmer can incorporate a low frequency (LF) RF transmitter or RFID reader/interrogator operating in the 50 to 135 KHz frequency range which would transmit a signal sufficient to penetrate right through the titanium housing of an AIMD and activate an embedded passive RF chip. The circuitry of the RF chip would be connected to telemetry circuits contained within the AIMD. For example, in the case of a pacemaker, the remote pacemaker programmer would send the RF signal as a wake-up call to turn on the AIMD telemetry receiving circuits so that the pacemaker could communicate with the remote AIMD programmer.

In a preferred embodiment, the RF chip is a four terminal RFID chip. RFID is widely used for inventory and article tracking. RFID operational protocols and frequencies have evolved worldwide. There are EPC and ISO standards, and also ANSI standards that cover the frequency band, forms of modulation, etc. In particular, the ISO 18,000 standards are particularly applicable to the present invention. For example, low frequency RFID systems operating below 135 kHz are governed by ISO 18,000-2. There are also standards governed by the standard body known as EPC Global which defines various UHF and HF RFID protocols. For example, EPC HF Class 1 covers 13.56 MHz. 13.56 MHz is also known as the RFID HF band and is covered by ISO 18,000-3. The use of a passive four terminal RFID tag for the present invention is preferred because the frequency allocations and other protocols have been worked out over the last couple of decades and have resolved themselves into these international standards.

The passive RFID tag draws no current at all from the AIMD battery. A passive RFID tag is entirely powered from the external reader/interrogator. This is what makes it possible to achieve such very low levels of current drop when the telemetry circuit is in its sleep mode. The only part of the AIMD transceiver or receiver that would be active at all is the electronic switch that is coupled to the RFID chip. In the case where this is a field effect transistor (FET) switch, the current draw would be exceedingly low. It is only when the RFID tag itself receives energy from an external source such as an RFID reader/interrogator, that it sends a pulse to activate the transceiver electronic switch, thereby waking up the entire AIMD telemetry transceiver circuitry.

The prior art Zarlink chip shortens a pacemaker battery life by over one month. The present invention would, in contrast, shorten a pacemaker battery life by only a portion of a single day.

There is another significant advantage to using a passive RFID tag to wake up the AIMD telemetry circuit. The RFID tag can be multifunctional. That is, when it receives a wake-up encoded pulse from an external reader/interrogator, it can act as the described telemetry wake-up trigger. However, by sending it an interrogation pulse, it can also be used to identify the make, model number, and/or identify MRI compatible features of the AIMD.

Figure 2:
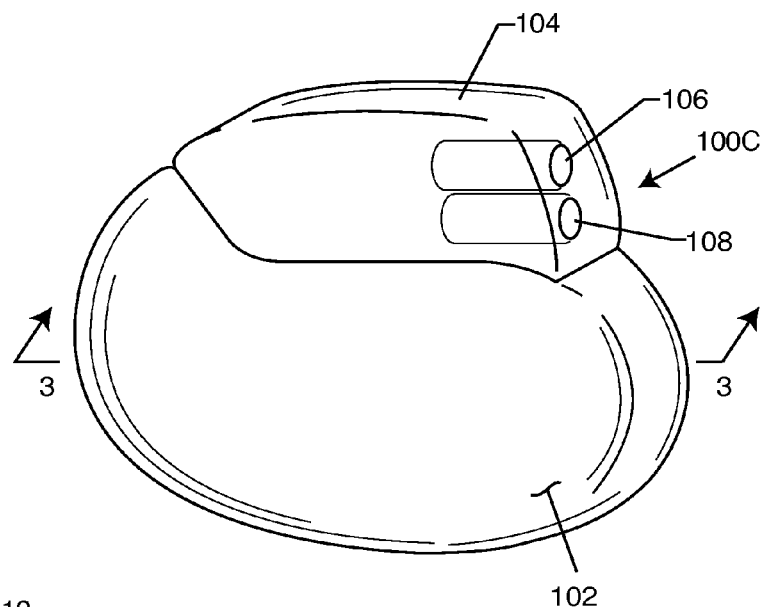
FIG. 2 is a prior art cardiac pacemaker.
Figure 3:
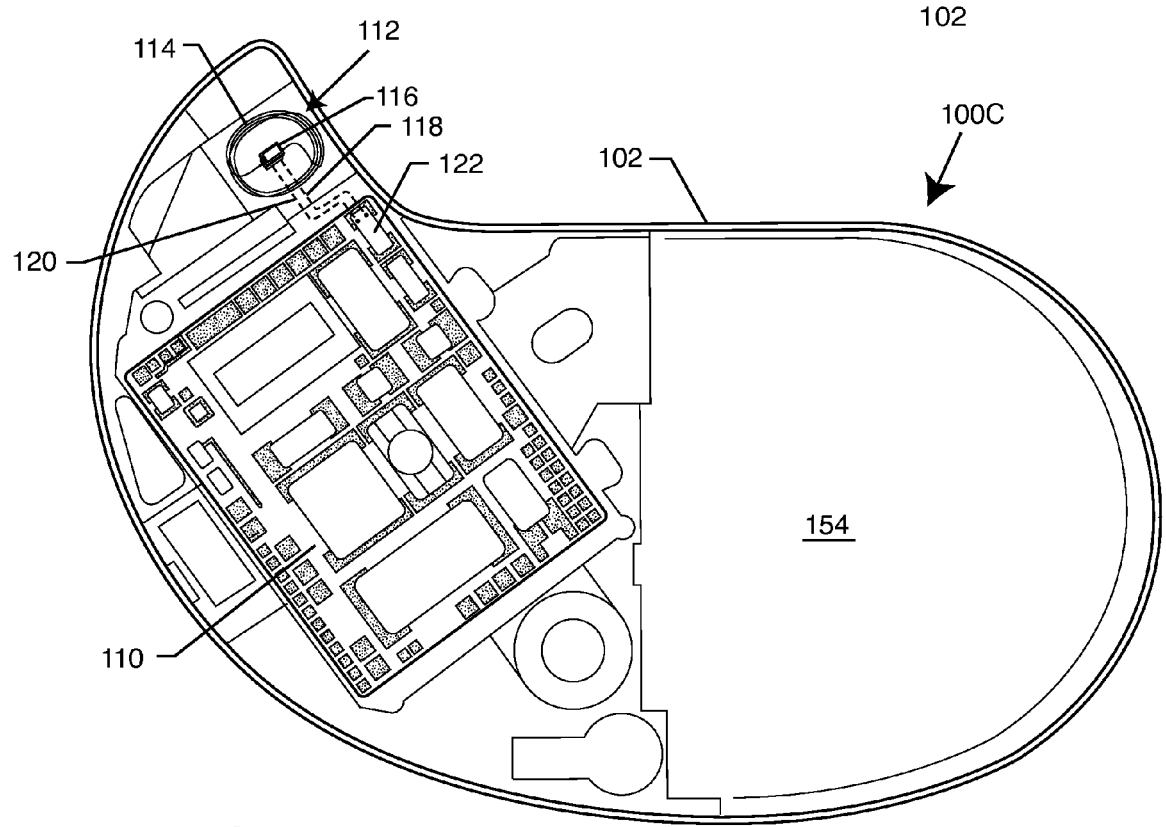
FIG. 3 is an enlarged cross-sectional view of the cardiac pacemaker taken generally along the line 3-3 from FIG. 2.
Figure 6:
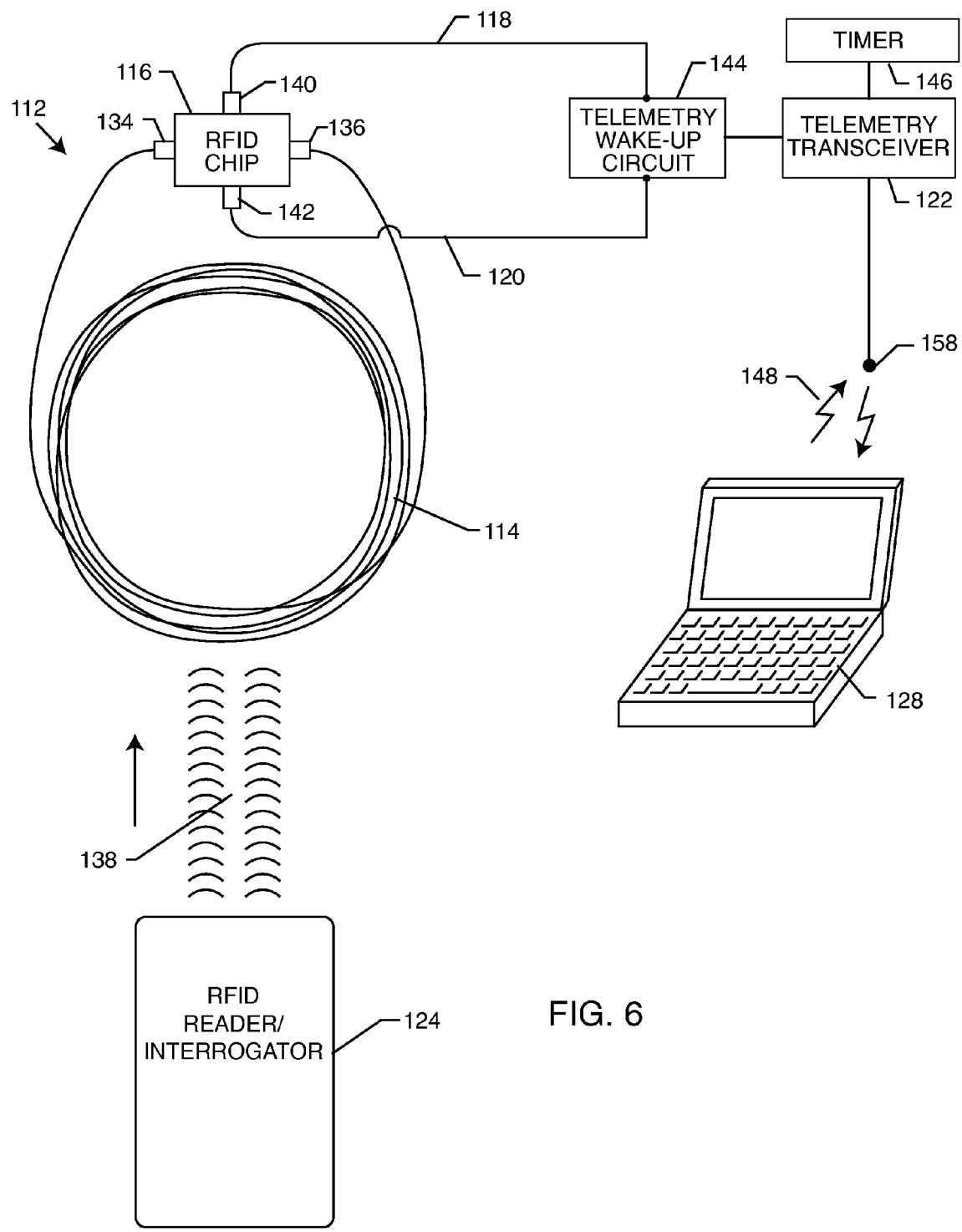
FIG. 6 is a diagrammatic view illustrating the component parts of the RF activated AIMD telemetry transceiver of the present invention.

FIG. 3 is a cross-sectional view taken generally along section 3-3 from FIG. 2. Shown is a circuit board or substrate 110 which contains many electronic components and microelectronic chips which enable the AIMD 100C to function. Also shown is an RF or RFID tag 112 which includes an antenna 114 and a four terminal RF or RFID chip 116. Two of the leadwires that are routed to the RFID chip 116 are connected to the antenna 114. There are also leadwires 118, 120 that are connected from the RFID chip 116 to AIMD telemetry transceiver circuitry 122 as shown. In a typical application, energy is received from a remote RFID reader/interrogator 124 (FIG. 6) and coupled to the RFID tag 112 antenna 114. A resonant circuit is formed between this antenna 114 and the RFID chip 116. Normally, a capacitor 126 (FIG. 7) would be placed in parallel with the antenna 114 to store energy. Once the RFID chip 116 receives the proper encoded signal from the reader/interrogator 124 (FIG. 7), it is activated and transmits a wake-up signal via leadwires 118, 120 to the AIMD telemetry transceiver 122. This wake-up pulse puts the telemetry transceiver 122 into its active mode so that it may communicate with its external/remote programmer 128 (FIG. 6). The remote programmer 128 may be the older style close-wanded telemetry low frequency magnetic coupling-type (FIG. 9) or it may be the newer RF distance telemetry-type (FIG. 8).

Referring once again to FIG. 3, the RFID tag 112 and its associated component antenna 114 and RFID chip 116 need not be biocompatible or hermetic. This is because they are disposed inside the overall electromagnetically shielded and hermetically sealed housing 102 of the AIMD 100C. There are advantages and disadvantages to this placement. The obvious advantage is the RFID tag 112 and all its associated components are in an environmentally inert environment and are never exposed to body tissue or body fluids. A disadvantage is the fact that the antenna 114 is disposed inside of the electromagnetically shielded housing 102 of the AIMD. This means, the antenna 114 can only effectively pick up low frequency RFID signals. These signals would typically be in the 50 to 135 kHz frequency range. The antenna 114 would be completely ineffective in picking up signals from an external RFID reader/interrogator 124 at HF (13.56 MHz) or higher frequencies. This is because the housing 102 of the AIMD would effectively shield such signals.

Figure 4:
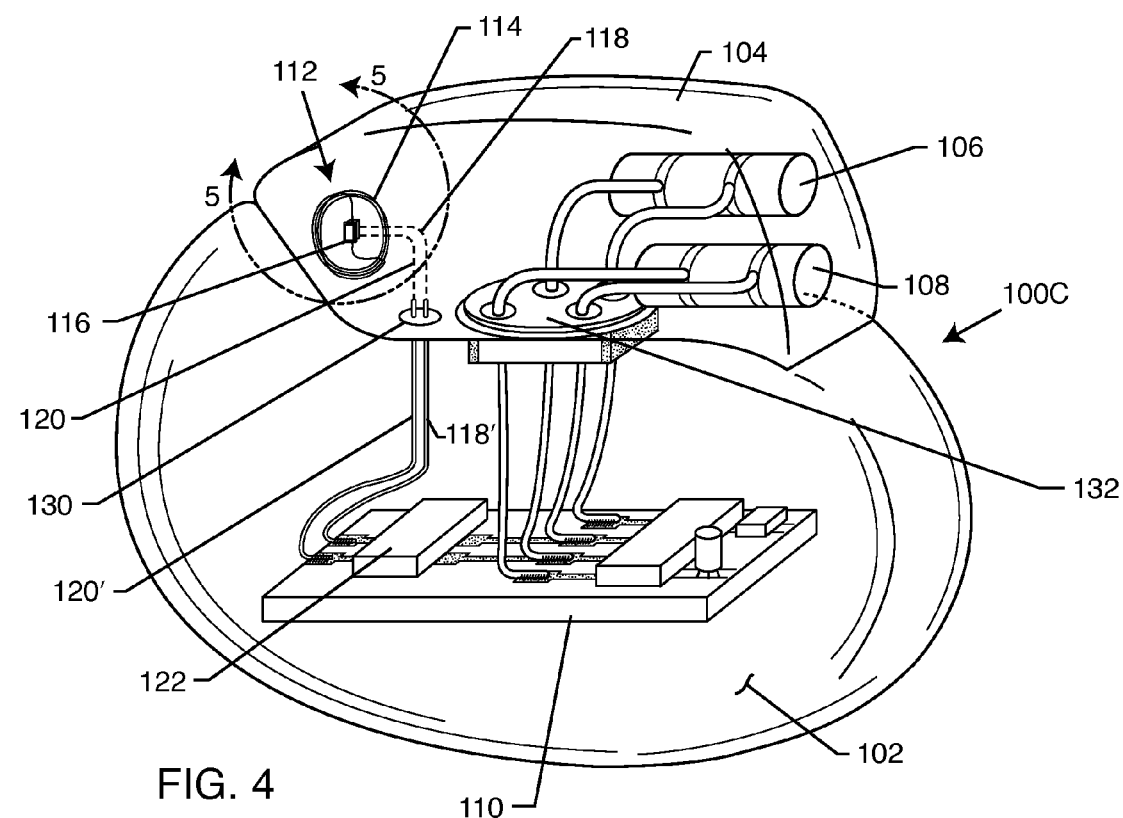
FIG. 4 is a perspective view of a typical cardiac pacemaker embodying the present invention, wherein the RF tag is disposed within the header block.

FIG. 4 illustrates a cardiac pacemaker 100C having an RFID tag 112 which is mounted in the AIMD plastic header block 104. In this application, the RFID antenna 114 would be more efficient because it is outside of the generally electromagnetically shielded housing 102 of the AIMD. Since the antenna 114 that is associated with the RFID tag 112 is now displaced within the plastic header block 104, it can more effectively pick up signals from the RFID reader/interrogator 124. In this case, the RFID frequency could still be in the low frequency range (LF) generally from 50 to 135 kHz, but it could also be in the HF (13.56 MHz) frequency range or even the UHF frequency bands. When the RFID tag 112 and its associated chip 116 and antenna 114 are placed in the header block 104, it is important that these components be resistant to body fluids. Over time, body fluids can penetrate through bulk permeability through the header block 104 plastic material. Accordingly, the antenna 114 of the RFID tag 112 must be made of biocompatible material, such as platinum, palladium, niobium and the like. In addition, the RFID chip 116 itself must be either biocompatible or placed within a hermetic package so it is also resistant to body fluids. See U.S. patent application Ser. No. 12/566,223, now U.S. application Pub. No. 2011/0071516, which is incorporated herein by reference. Leadwires 118 and 120 should also be biocompatible up to the point where they are connected to the hermetic seal 130. It will be apparent to those skilled in the art. that the hermetic seal 130 for the RFID tag 112 could be incorporated within the overall hermetic seal 132 which is coupled to the IS-1 connectors 106, 108 and. internal electronic circuits. Leadwires 118 and 120 are routed to leadwires 118' and 120' within the AIMD housing 102 and are connected to the telemetry transceiver 122 which is disposed on a circuit board 110.

Figure 5:
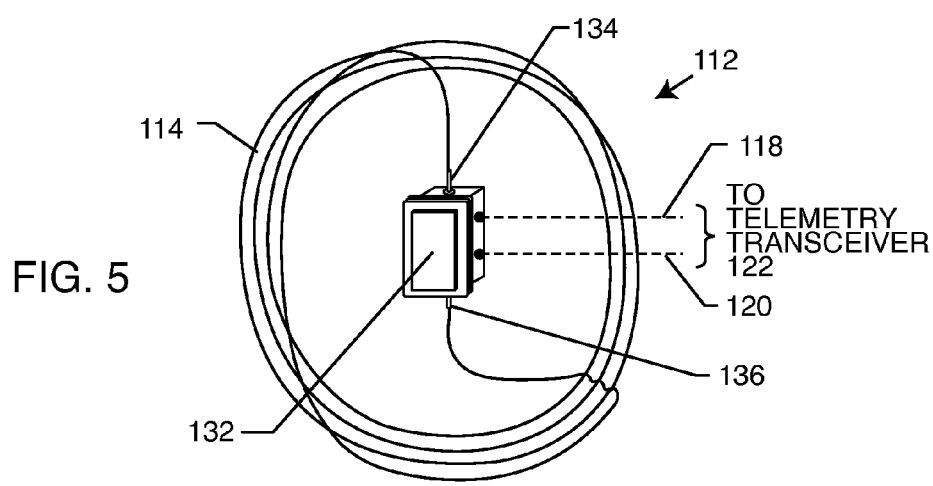
FIG. 5 is an enlarged perspective view of the RF tag taken generally about the line 5-5 from FIG. 4.

FIG. 5 shows that the RFID tag 112 of FIG. 4 consists of antenna structure 114 and a hermetically sealed package 132 in which the RFID chip 116 is disposed. Terminals 134 and 136 are connected to the RFID tag's antenna 114. Leadwires 118 and 120 are routed to the telemetry transceiver 122 which is located inside of the electromagnetically shielded and hermetically sealed AIMD housing 102.

Referring once again to FIG. 4, one can see that the antenna 114 of the RFID tag 112 is disposed outside of the hermetic and electromagnetically sealed housing 102 of the AIMD 100C. In an alternative embodiment, the RFID chip 116 could be disposed inside of the housing 102 of the AIMD, for example, placed on the circuit board 110 adjacent to transceiver chip 122. In this embodiment, the antenna 114 of the RFID tag 112 would still be disposed outside of the AIMD shielded housing 102 wherein its associated RFID chip and energy storage capacitor 126 are disposed inside the hermetically sealed housing 102.

FIG. 6 is a diagrammatic view illustrating how the RFID activated AIMD telemetry transceiver of the present invention would operate. Shown is an RFID reader/interrogator 124. It may be a standalone unit, such as a hand-held RFID reader (FIGS. 8-10) or it could be incorporated within or adjacent to the AIMD remote programmer 128 (FIG. 11). A signal or pulse 138 is produced when the RFID reader/interrogator 124 is activated which couples energy to tuned antenna 114 of the RFID tag 112. This couples energy to terminals 134 and 136 of the RFID chip 116 which activates the RFID chip. The RFID chip 116 stores this energy in a capacitor (not shown) which then transmits a wake-up pulse via terminals 140 and 142 to the telemetry wake-up circuit 144. The telemetry wake-up circuit 144 then turns power on to the AIMD telemetry transceiver 122, placing it into an active telemetry mode. Also shown is an optional timer 146 which will turn off the telemetry transceiver 122 and put it back into its sleep mode after a predetermined amount of time. An alternative to the timer 146 is that a second activation of the RFID reader/interrogator 124 would cause the RFID chip 116 to once again be activated so that it sends a toggle pulse back to the telemetry wake-up circuit 144. This would unlatch or turn off the telemetry transceiver 122 and put it back into its sleep mode. There is a third method of putting the telemetry transceiver 122 back into its sleep mode and that would be by sending a special pulse 148 from the remote programmer 128 which would instruct the telemetry transceiver 122 to go back into its sleep mode.

Figure 7:
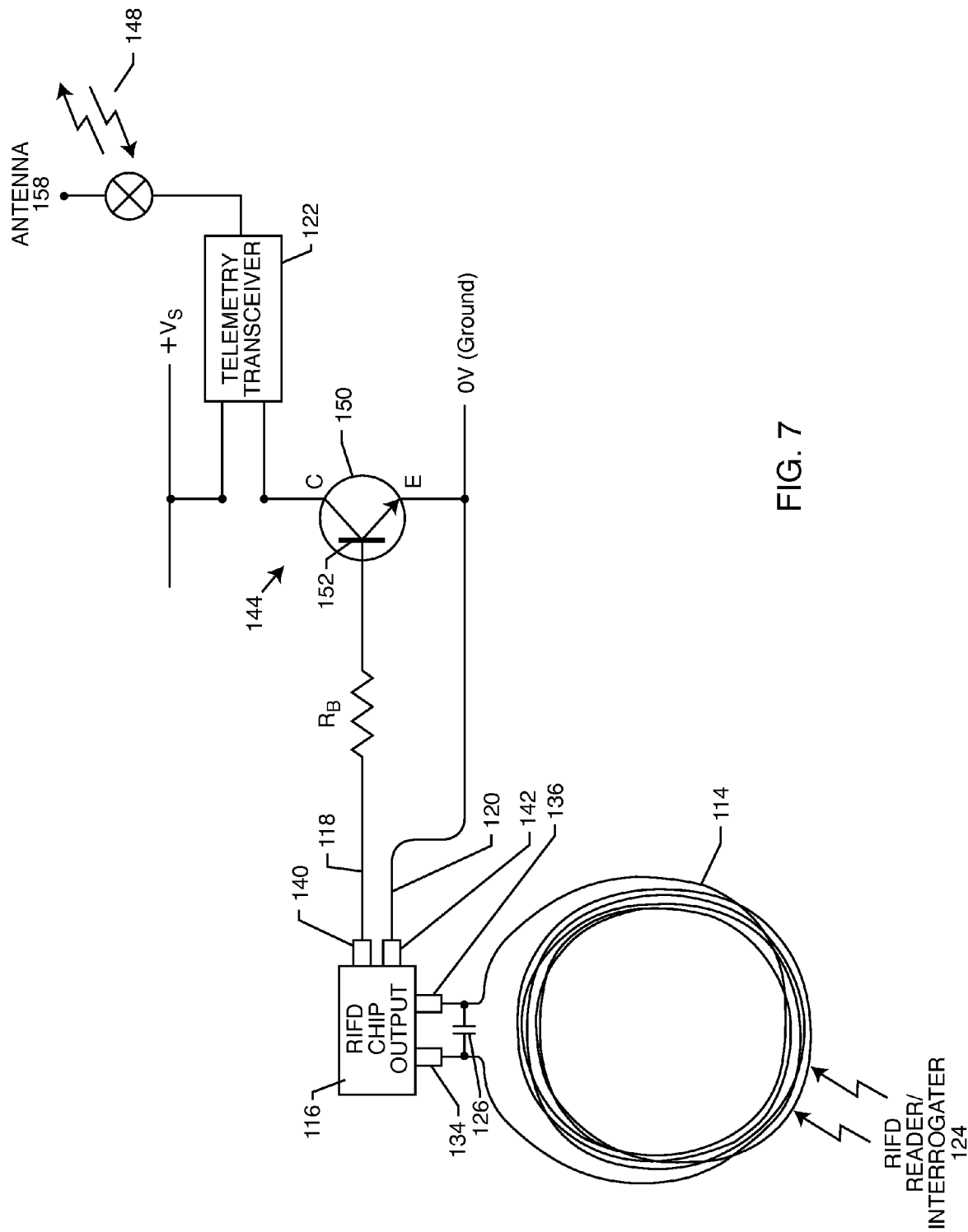
FIG. 7 is an electrical schematic of the circuitry illustrated in FIG. 6.
Figure 8:
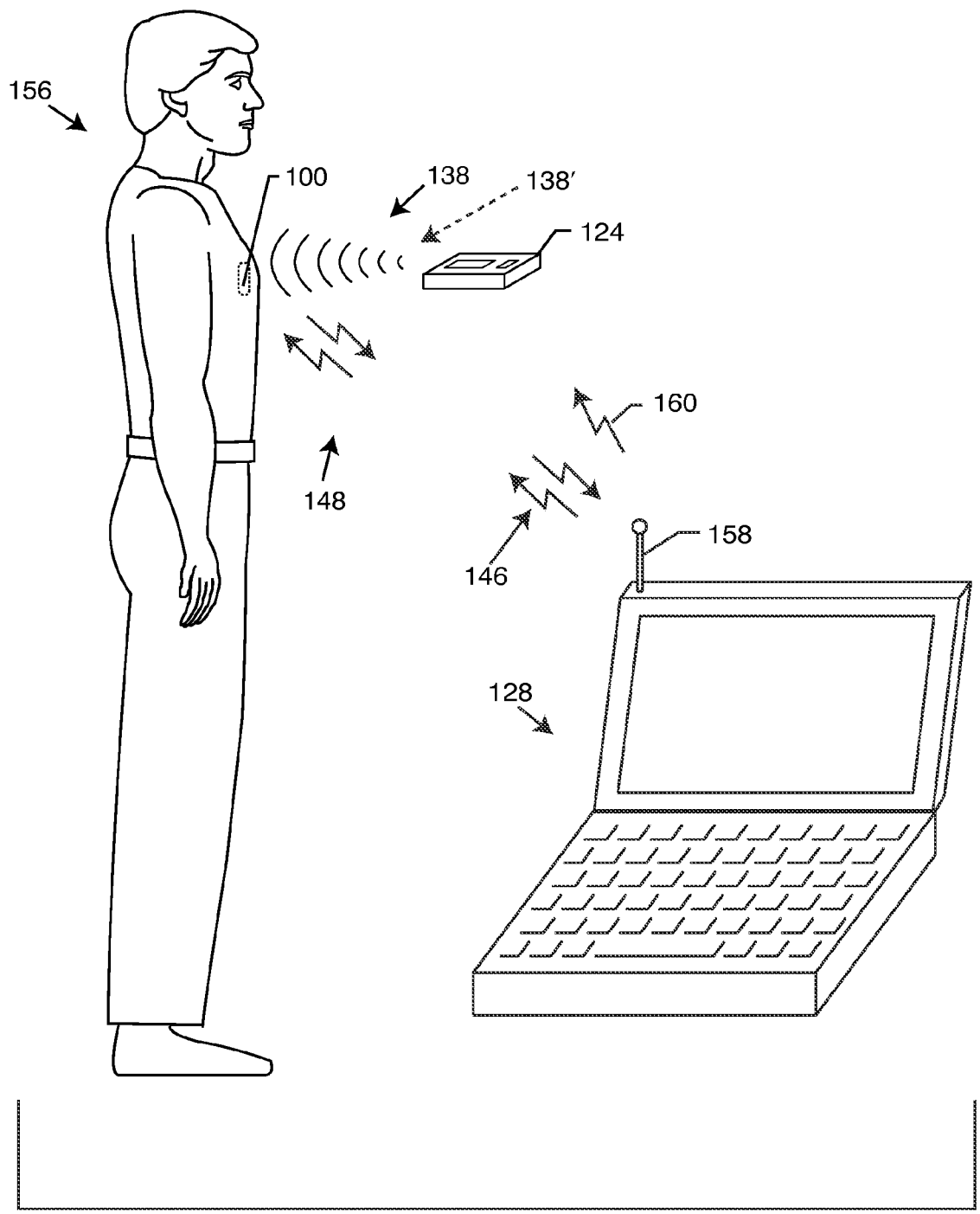
FIG. 8 is a system diagram illustrating operation of the present invention.

FIG. 7 is an electrical schematic diagram of the system of FIG. 6, illustrating the components of the telemetry wake-up circuit 144. Shown, in this case, is a bipolar junction transistor (BJT) which is also known as a N-P-N transceiver switch 150. The transistor 150 base 152 receives a signal from the RFID chip 116 from terminals 140 and 142 through leadwires 118 and 120. This results in a very low voltage drop between the transistor 150 collector C and the emitter E. This effectively connects the telemetry transceiver 122 to voltage source $V_s$ and to the ground reference voltage 0V. This activates the telemetry transceiver 122 which is shown connected to its antenna 158 so that it can receive and transmit information from the AIMD remote programmer 128 (FIG. 6). The voltage source $V_s$ is normally supplied from the AIMD internal battery 154 (FIG. 3). The N-P-N transceiver switch 150 is illustrative of any type of microelectronic switch. These can include a bipolar junction transistor (BJT), a field effect transistor (FET), a metal oxide substrate field effect transistor (MOSFET), a microelectronic mechanical switch (MEMS), a unijunction transistor switch, a silicon-controlled rectifier (SCR) switch, a PIN diode, a P-N junction transistor switch, a P-N-P transistor switch, or any type of N-P-N transistor switch. In general, the RFID chip 116 of the present invention contains at least four terminals. Two of these terminals 134, 136 are reserved for connection to the antenna 114 and its associated resonating capacitor 126. The other two or more terminals 140, 142 are for connection to AIMD telemetry transceiver circuits 118, 120 in order to provide both wake-up and go back to sleep pulses.

FIG. 8 illustrates the operation of the present invention. Shown is a human patient 156 who has an AIMD 100. In its normal operating mode, the AIMD's telemetry transceiver circuits would be in a sleep or quiescent low battery drain mode. A signal 138 is transmitted by an RFID reader/interrogator 124. This pulse 138 is coupled to the RFID tag 112 that is associated with the AIMD 100. The RFID signal 138 then wakes up the AIMD's telemetry transceiver 122. It is at this point that the remote programmer 128 can form a two-way communication link between the AIMD 100 and the programmer 128. In the case shown in FIG. 8, the remote programmer 128 has an antenna 158, which is an RF antenna. This forms a so-called distance telemetry link between the remote programmer 128 and the AIMD 100. This typically operates at high frequency. One popular set of frequencies is the MICS band operating in the 402 to 405 MHz frequency range. As previously described, the telemetry transceiver of the AIMD 100 can be put back into its wake-up mode in a number of ways, including an internal timer circuit 146, receipt of a second type of RFID pulse 138' which will instruct the RFID chip 116 to unlatch the telemetry wake-up circuit thereby putting the telemetry transceiver back into its sleep mode, or even by transmission of a special pulse sequence 160 from the remote programmer 128 which instructs the transceiver 122 to go back into its sleep mode.

Figure 9:
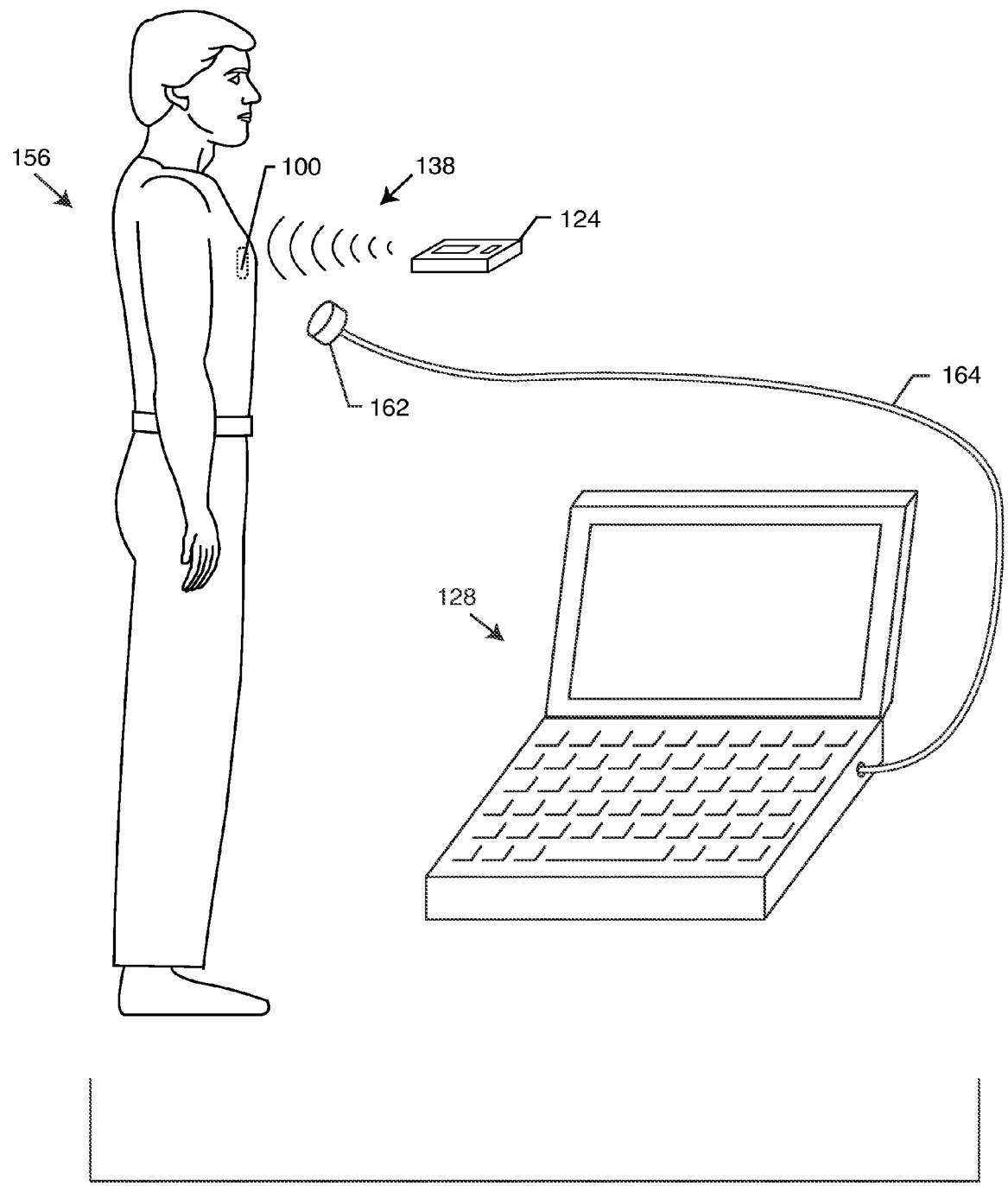
FIG. 9 is a system illustration similar to FIG. 8, except that an older style of external program is shown including a wand which is placed over the patient's AIMD.

FIG. 9 is very similar to FIG. 8, except that an older style of remote programmer 128 is shown which includes a wand 162 which is placed over the patient's AIMD 100. The wand 162 is generally connected through leads 164 to the remote programmer 128. This type of wanded telemetry involves a close coupled low frequency magnetic link between an antenna in the wand 162 and an associated multi-turn loop antenna associated with the AIMD 100. Generally, the wand 162 would be placed either very close to or directly on the patient's chest directly over the AIMD 100. This is the case for a cardiac pacemaker 100C. Of course, the AIMD 100 could be located anywhere within the human body in which case the wand 162 would have to be placed over it. The system of FIG. 9 operates in all ways as previously described in connection with FIG. 8.

Figure 10:
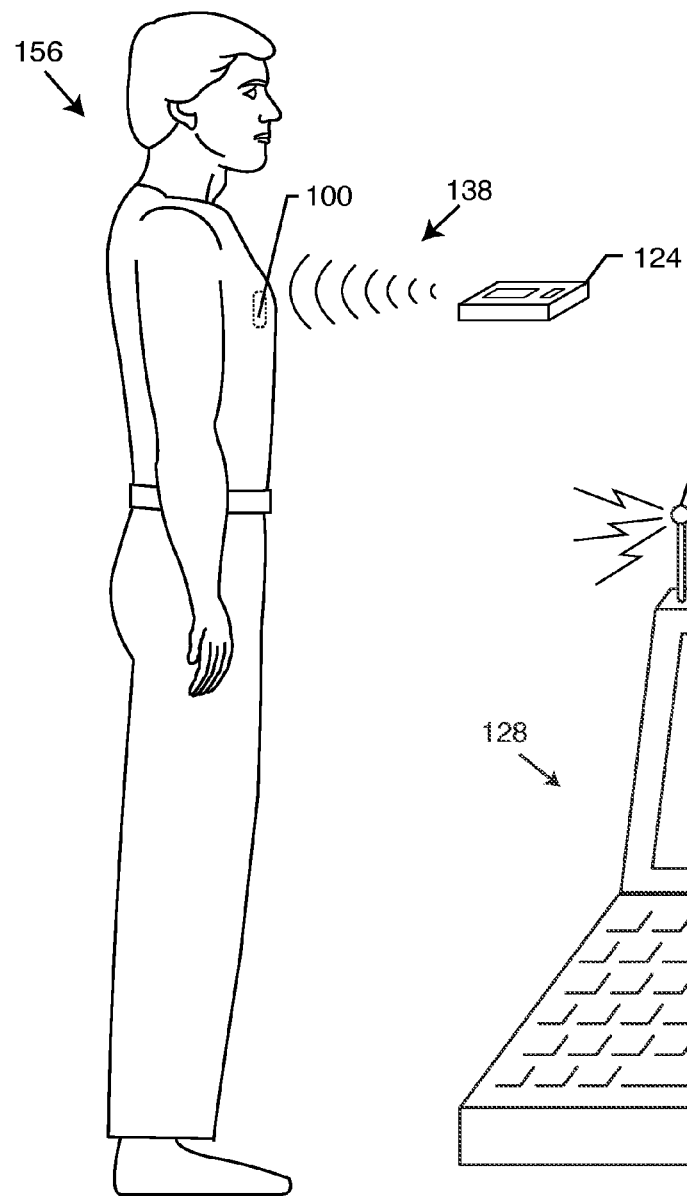
FIGS. 10 and 11 are similar to FIGS. 8 and 9, illustrating that the RFID reader/interrogator can be incorporated either within or connected to the AIMD external programmer.
Figure 11:
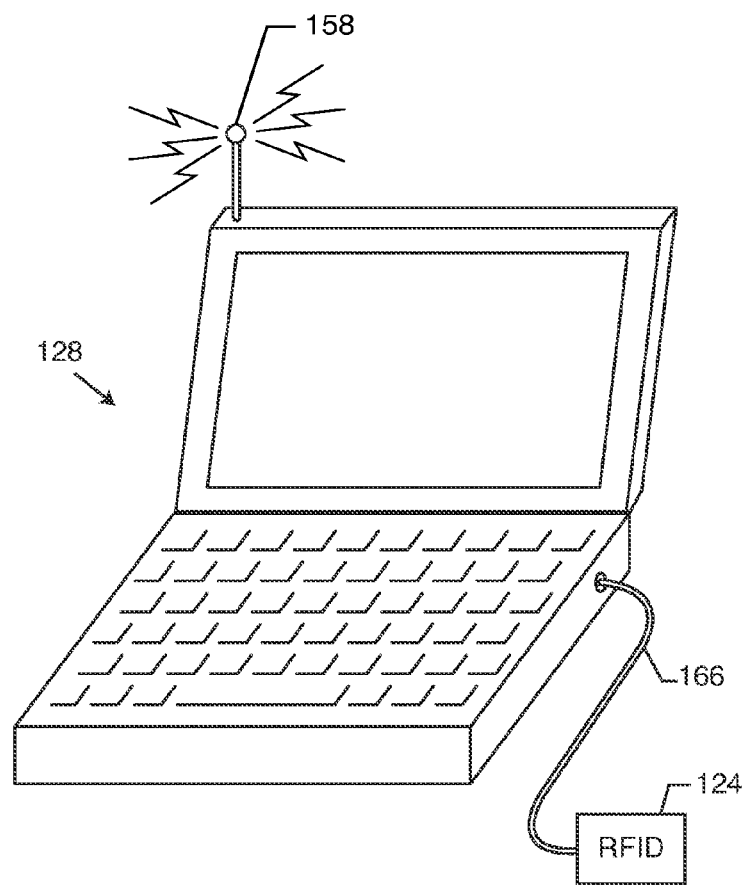

FIGS. 10 and 11 are similar to FIGS. 8 and 9, however in this case, the RFID reader 124, which is illustrated in FIG. 10, can be incorporated either within or connected to the AIMD remote programmer 128. This eliminates the need to have an external portable RFID reader 124, which would be about the size of a garage door opener. The problem with a small reader around a hospital or operating theater is it is easily misplaced or lost. Accordingly, it is a feature of the present invention that the RFID reader 124 that activates the RFID tag 112 may be built inside of or connected via leads 166 to the AIMD remote programmer 128.

From the foregoing, it will be appreciated that the present invention relates to an RF-activated AIMD telemetry transceiver which includes a telemetry transceiver associated with the AIMD, an RF tag associated with the telemetry transceiver, and a telemetry wake-up circuit electrically disposed between the telemetry transceiver and the RF tag. The RF tag comprises a passive RF chip and an antenna. Preferably, the antenna is biocompatible and the RF chip is disposed within a hermetic package. The telemetry transceiver has an active telemetry mode wherein a telemetry transceiver is powered by the AIMD, and a sleep mode. The telemetry wake-up circuit is responsive to a signal from the RF tag to place the telemetry transceiver into the active telemetry mode.

Although several embodiments of the invention have been described in some detail for purposes of illustration, various modifications may be made without departing from the spirit and scope of the invention. Accordingly, the invention is not to be limited, except as by the appended claims.

What is claimed is:
1. An active implantable medical device (AIMD), comprising:
   a) a telemetry transceiver that is powerable by the AIMD, the transceiver having an active telemetry mode when it is powered by the AIMD and a sleep mode when it is not being powered by the AIMD; and
   b) a passive RF tag comprising at least four terminals, wherein a first terminal and a second terminal are connected to opposite ends of an RF antenna, a third terminal is electrically connected to a first connection of a wake-up circuit, and a fourth terminal is electrically connected to a second connection of the wake-up circuit; and c) an electrical connection from the wake-up circuit to the transceiver, d) wherein the RF tag is configured to receive an interrogation signal from a remote location via the RF antenna and then transmit a wake-up signal to the wake-up circuit via the third and fourth terminals, and e) wherein the wake-up circuit is configured to then connect the transceiver to the AIMD power source to thereby activate the transceiver from the sleep mode to the active telemetry mode for receiving information from the remote location and transmitting information from the AIMD to the remote location for subsequent use of the information.

2. The AIMD of claim 1, wherein the RF tag comprises a passive RF chip and the RF antenna.

3. The AIMD of claim 2, wherein the RF chip comprises a passive RFID chip.

4. The AIMD of claim 1 wherein the transceiver draws less than 25,000 nanoamperes from the AIMD during the sleep mode.

5. The AIMD of claim 1 wherein the transceiver draws less than 500 nanoamperes from the AIMD during the sleep mode.

6. The AIMD of claim 1 or 5, wherein the wake-up circuit comprises a microelectronic switch.

7. The AIMD of claim 6, wherein the microelectronic switch is selected from the group consisting of a bipolar junction transistor (BJT) switch, a field effect transistor (FET) switch, a metal oxide substrate field effect transistor (MOSFET) switch, a microelectronic mechanical switch (MEMS), a unijunction transistor switch, a silicon-controlled rectifier (SCR) switch, a PIN diode switch, a P-N junction transistor switch, a P-N-P transistor switch, and a N-P-N junction switch.

8. The AIMD of claim 1, including a timing circuit for switching the transceiver from the active telemetry mode back to the sleep mode.

9. The AIMD of claim 8 wherein the timing circuit is re-set responsive to the wake-up signal from the RF tag to place the transceiver into the active telemetry mode.

10. The AIMD of claim 1, wherein the transceiver includes a sleep mode circuit responsive to a signal from the RF tag or a remote RF or inductive low frequency magnetic coupling source, for switching the transceiver from the active telemetry mode to the sleep mode.

11. The AIMD of claim 1 wherein the RF antenna comprises a biocompatible antenna.

12. The AIMD of claim 1 wherein the RF tag is disposed within a hermetic package.

13. The AIMD of claim 12 wherein the hermetic package comprises a housing for the AIMD.

14. The AIMD of claim 13, wherein the RF antenna is disposed external of the hermetic package.

15. The AIMD of claim 1 wherein the RF tag is disposed within a header block of the AIMD.

16. The AIMD of claim 1 wherein in the active telemetry mode, the transceiver is configured to receive information from the remote location regarding reprogramming of the AIMD.

17. The AIMD of claim 1 wherein with the RF tag housed inside the AIMD, the RF tag is configured to receive the interrogation signal having a frequency of from about 50 kHz to about 135 kHz.

18. An active implantable medical device (AIMD), comprising:

a) a telemetry transceiver that is powerable by the AIMD, the transceiver having an active telemetry mode when it is powered by the AIMD and a sleep mode when it is not being powered by the AIMD; and b) a passive RF tag comprising at least four terminals, wherein a first terminal and a second terminal are connected to opposite ends of an RF antenna, a third terminal is electrically connected to a first connection of a N-P-N junction switch, and a fourth terminal is electrically connected to a second connection of the N-P-N junction switch; and c) an electrical connection from the N-P-N junction switch to the transceiver, d) wherein the RF tag is configured to receive an interrogation signal from a remote location via the RF antenna and then transmit a wake-up signal to the N-P-N junction switch via the third and fourth terminals, and e) wherein the N-P-N junction switch is configured to then connect the transceiver to the AIMD power source to thereby activate the transceiver from the sleep mode to the active telemetry mode for receiving information from the remote location and transmitting information from the AIMD to the remote location for subsequent use of the information.

19. The AIMD of claim 18 wherein in the active telemetry mode, the transceiver is configured to receive information from the remote location regarding reprogramming of the AIMD.

20. The AIMD of claim 18 wherein with the RF tag housed inside the AIMD, the RF tag is configured to receive the interrogation signal having a frequency of from about 50 kHz to about 135 kHz.

21. A system for transmitting information to and from an active implantable medical device. (AIMD), comprising:

a) a telemetry transceiver powerable by the AIMD, the transceiver having an active telemetry mode when it is powered by the AIMD and a sleep mode when it is not being powered by the AIMD, wherein the transceiver comprises:

i) a passive RF tag comprising at least four terminals, wherein a first terminal and a second terminal are connected to opposite ends of an RF antenna, a third terminal is electrically connected to a first connection of a wake-up circuit, and a fourth terminal is electrically connected to a second connection of the wake-up circuit; and ii) an electrical connection from the wake-up circuit to the transceiver;

b) a RF transmitter that is not electrically connected to the transceiver; and c) programmer that is not electrically connected to the transceiver;

d) wherein the RF tag is configured to receive an interrogation signal from the RF transmitter via the RF antenna and then transmit a wake-up signal to the wake-up circuit via the third and fourth terminals, and e) wherein the wake-up circuit is configured to then connect the transceiver to the AIMD power source to thereby activate the transceiver from the sleep mode to the active telemetry mode for receiving information from the programmer and transmitting information from the AIMD to the programmer for subsequent use of the information.

22. The AIMD of claim 21 wherein the RF transmitter comprises an RFID reader/interrogator.

23. The AIMD of claim 21 wherein with the transceiver in the active telemetry mode, the transceiver is configured to receive information from and transmit information to the programmer comprising a remote RF or inductive low frequency magnetic coupling source.

24. The AIMD of claim 21 wherein the RF transmitter is electrically connected to the programmer.

25. The AIMD of claim 24, wherein the RF transmitter is disposed within or tethered to the programmer.

26. The AIMD of claim 21 wherein in the active telemetry mode, the transceiver is configured to receive information from the remote location regarding reprogramming of the AIMD.

27. The AIMD of claim 21 wherein with the RE tag housed inside the AIMD, the RE tag is configured to receive the interrogation signal having a frequency of from about 50 kHz to about 135 kHz.

\* \* \* \* \*

UNITED STATES PATENT AND TRADEMARK OFFICE
CERTIFICATE OF CORRECTION

PATENT NO. : 8,761,895 B2  Page 1 of 1
APPLICATION NO. : 12/719630
DATED : June 24, 2014
INVENTOR(S) : Robert A. Stevenson et al.

It is certified that error appears in the above-identified patent and that said Letters Patent is hereby corrected as shown below:

In The Claims

Column 9, line 18 (Claim 2, line 2) delete "RE" and insert --RF--

Column 9, line 50 (Claim 12, line 1) delete "RE" and insert --RF--

Column 9, line 62 (Claim 17, line 1) delete "RE" and insert --RF--

Column 9, line 63 (Claim 17, line 2) delete "RE" and insert --RF--

Column 10, line 14 (Claim 18, line 16) delete "RE" and insert --RF--

Column 10, line 29 (Claim 20, line 1) delete "RE" and insert --RF--

Column 10, line 30 (Claim 20, line 2) delete "RE" and insert --RF--

Column 10, line 50 (Claim 21, line 17) delete "RE" and insert --RF--

Column 10, line 51 (Claim 21, line 19) after "c)" insert --a--

Column 10, line 53 (Claim 21, line 21) delete "RE" and insert --RF--

Column 11, line 12 (Claim 27, line 1) delete "RE" and insert --RF--

Column 11, line 13 (Claim 27, line 2) delete "RE" and insert --RF--

Signed and Sealed this
Twenty-fourth Day of February, 2015

Michelle K. Lee
*Deputy Director of the United States Patent and Trademark Office*